United States Patent [19]

Thyen

[11] 4,014,434
[45] Mar. 29, 1977

[54] FOLDERS AND INTEGRAL LOCK THEREFOR

[75] Inventor: Eberhard H. Thyen, Middlesex, N.J.
[73] Assignee: Ethicon, Inc., Somerville, N.J.
[22] Filed: Sept. 3, 1975
[21] Appl. No.: 610,011
[52] U.S. Cl. .............................. 206/63.3; 206/491; 229/84; 229/87 R
[51] Int. Cl.² ........................................ A61L 17/02
[58] Field of Search .......... 229/82, 84, 87 R, 87 A, 229/87 S; 206/63.3, 491

[56] References Cited

UNITED STATES PATENTS

| | | | |
|---|---|---|---|
| 649,768 | 5/1900 | Sherriff | 229/84 X |
| 806,228 | 12/1905 | Young | 229/84 X |
| 1,103,742 | 7/1914 | Dammon | 229/87 S |
| 1,658,981 | 2/1928 | Galbraith et al. | 229/84 X |
| 2,027,119 | 1/1936 | Ritter | 229/87 A |
| 2,437,934 | 3/1948 | Brink | 229/84 |
| 2,692,676 | 10/1954 | Grover | 206/63.3 |
| 2,826,296 | 3/1958 | Mullinix | 229/87 A X |
| 3,206,018 | 9/1965 | Lewis et al. | 206/63.3 |

Primary Examiner—Stephen P. Garbe
Attorney, Agent, or Firm—Wayne R. Eberhardt

[57] ABSTRACT

Folders of paper or similar foldable material which comprise at least three panels adapted to be folded in an overlapping relationship are provided with integral means for interlocking two of the panels to maintain the folder in the folded construction. The locking means comprise a tab extending from the edge of the outer end panel and a cooperating locking slot in the adjacent underlying panel adapted to receive the tab by forced bypass interlocking. The non-locking panels are provided with relief slots in the locking area to facilitate the forced bypass interlocking of the tab and lock-slot in the locking panels. Such folders are useful for packaging sutures.

6 Claims, 11 Drawing Figures

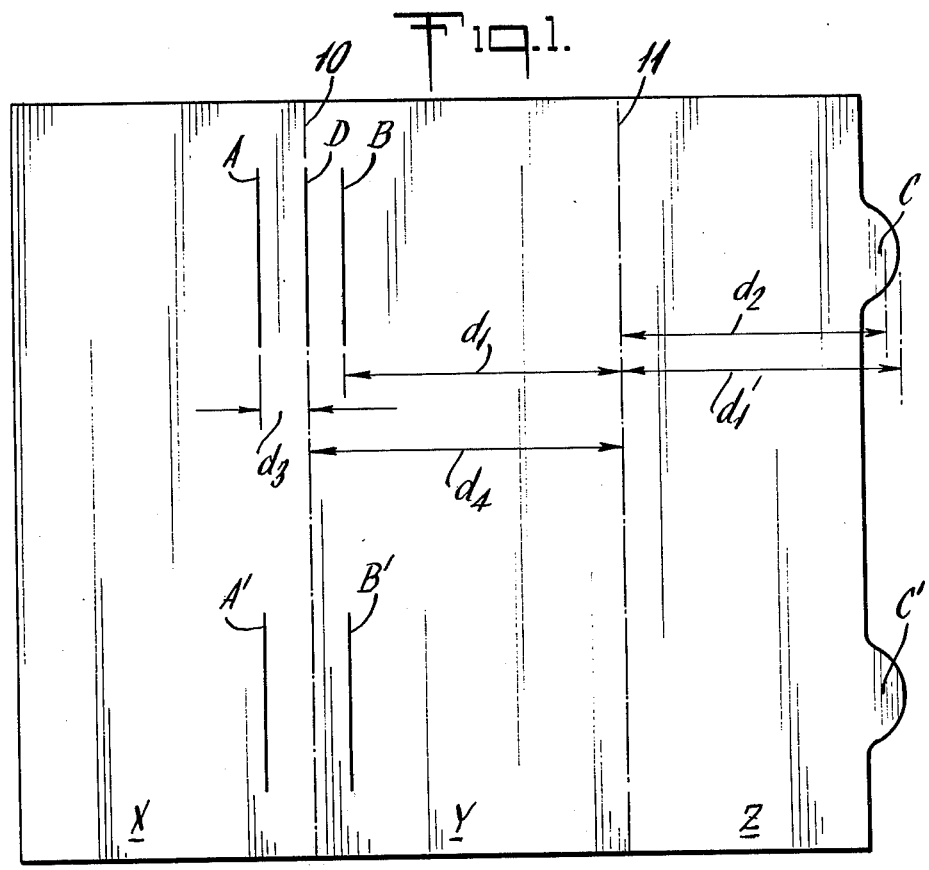
Fig. 1.
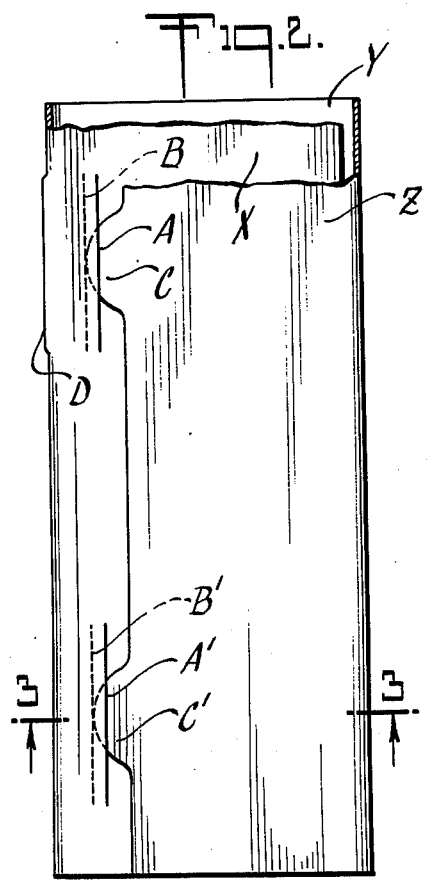
Fig. 2.
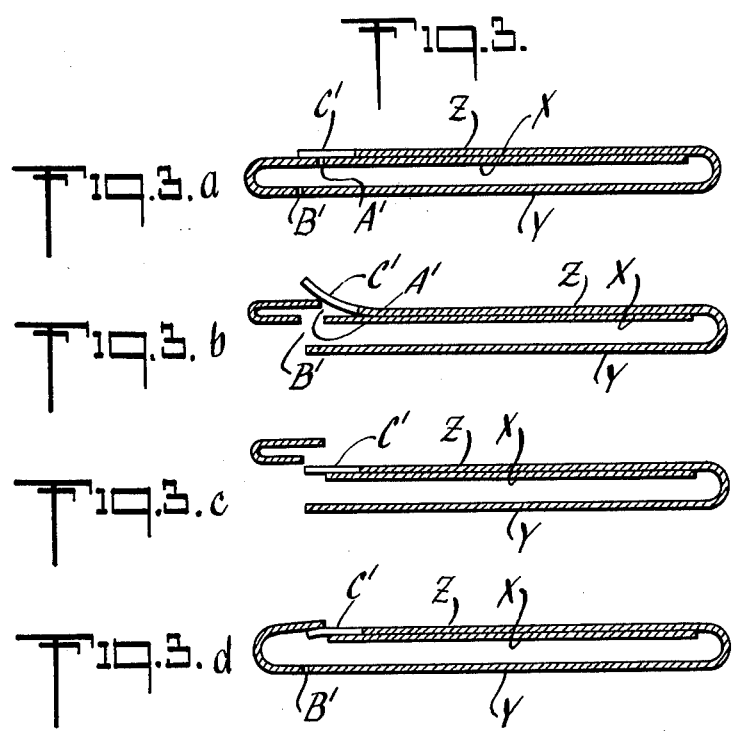
Fig. 3.a
Fig. 3.b
Fig. 3.c
Fig. 3.d

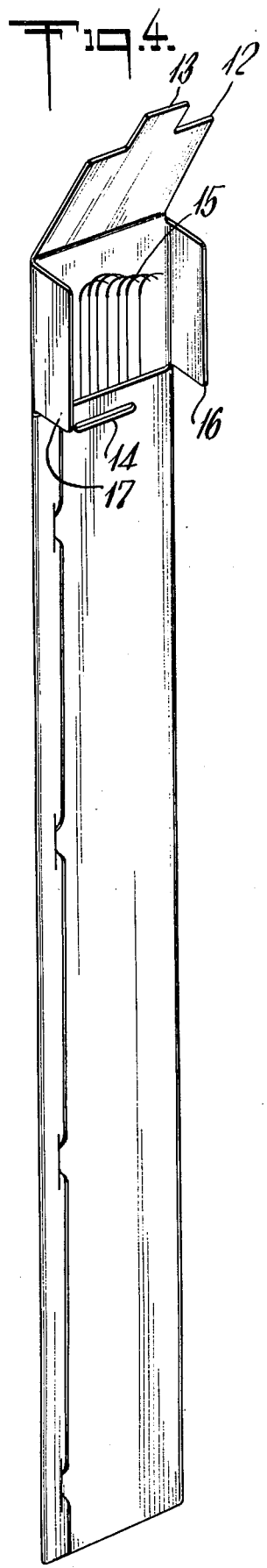
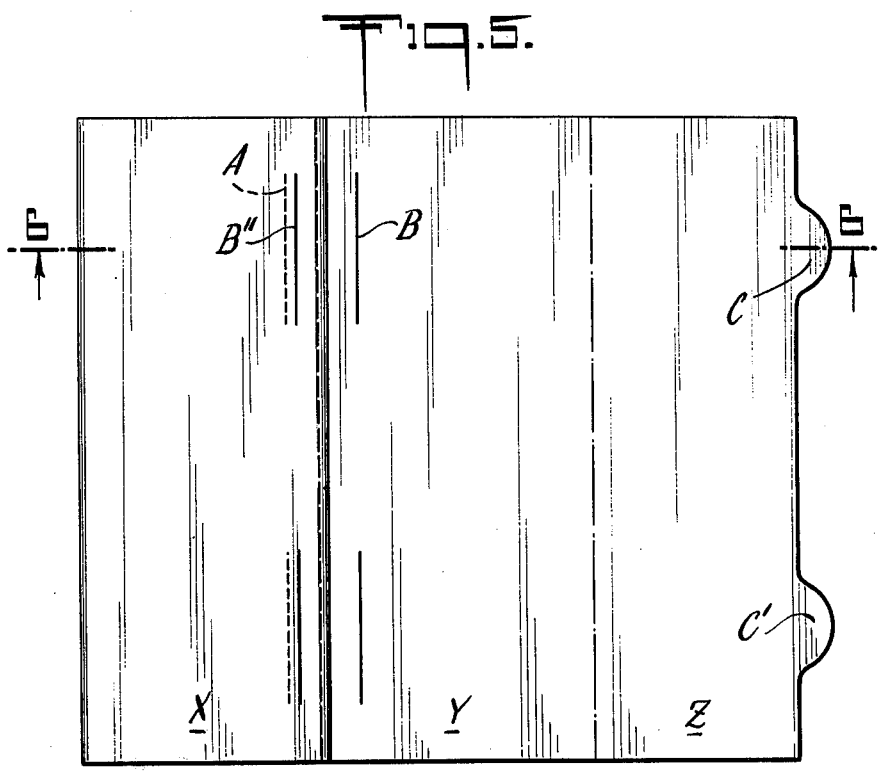
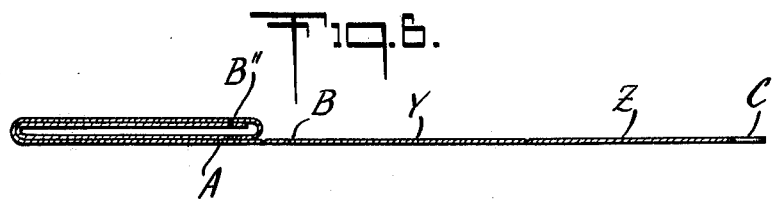
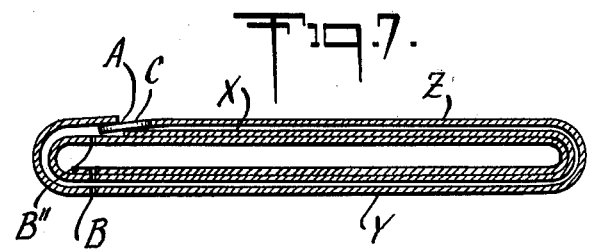

FOLDERS AND INTEGRAL LOCK THEREFOR

BACKGROUND OF THE INVENTION

1. Field of the Invention

This invention relates to folders of paper or similar foldable, relatively stiff materials. More particularly, this invention relates to an integral tab and slot locking means for maintaining folders in a folded construction and to folders, particularly suture package folders, utilizing this locking mechanism.

2. Description of Prior Art

Paper folders are used to package a variety of small items where the package is not required to provide a great deal of structural strength or rigidity to contain the item. It is, for example, common practice to package many types of surgical suture materials in heavy paper or paper-board folders which are then sterilized and hermetically sealed in an outer plastic wrapper. This invention is particularly concerned with an improvement in such folders.

Paper folders can be secured in the folded configuration by external means such as stapling, gluing, or taping, or they may be secured by integral means such as by providing the folder with a locking tab and slot combination. For the sake of economy and ease of assembly, it is generally preferable to use integral folder-locking means. In modern packaging systems, it is further desirable that the locking means be adaptable to machine closure as well as manual closure.

In conventional folders utilizing a tab and slot locking system, it is necessary to carefully insert the tab into the slot. Although such closures have been automated, automation is difficult because precise alignment of the tab and slot is necessary during closure. It is an object of the present invention to provide a folder with a tab and slot locking means suitable for rapid manual or automatic machine closing. It is a further object of this invention to provide an improved suture folder utilizing a tab and slot locking means. These and other objects of the invention will be apparent from the ensuing description and claims.

SUMMARY

Folders of the present invention are comprised of at least three panels, a center panel and two end panels folded inwardly over the center panel so that one end panel overlaps a portion of the opposite end panel to provide an enclosed center space with open ends. The edge of the outer end panel is provided with tabs which extend over the underlying panel, and the underlying panel is provided with a slot underlying the tab of the outer panel and adapted to receive the tab by forced bypass entry. The center panel of the three-panel folder is provided with a relief slot aligned with the end of the tab to facilitate forced bypassing of the tab and immediate underlying slot. In folders comprising more than three panels, all non-locking panels are provided with relief slots corresponding to the relief slot in the center panel of a three-panel folder.

DESCRIPTION OF DRAWINGS

FIG. 1 is a plan view of a three-panel folder in an open position;

FIG. 2 is a partially cut away plan view of the folder of FIG. 1 in a folded and locked construction;

FIG. 3 is a series of cross-sectional views through the locking means of the folder of FIG. 2 along line 3—3 illustrating the forced bypass locking method;

FIG. 4 is a view in perspective of a suture folder utilizing the forced bypass folder locking means of the present invention;

FIG. 5 is a plan view of a multipanel folder wherein the underlying end panel comprises a plurality of folded panels;

FIG. 6 is a cross-sectional view of the folder of FIG. 5 along line 6—6;

FIG. 7 is a cross-sectional view of the folder of FIG. 5 in a completely folded and locked construction.

DESCRIPTION OF PREFERRED EMBODIMENTS

Folders of the present invention are comprised of at least one center panel with two end panels adapted to be folded inwardly over the center panel with one end panel partially overlapping the other. The outer end panel is provided with one or more tabs extending beyond the edge of the panel and the underlying end panel is provided with a corresponding number of slots adapted to receive the tabs of the outer end panel by forced bypassing. The center panel is provided with a corresponding number of relief slots aligned with the end of the tab of the outer end panel when the folder is in its folded configuration to facilitate the forced bypass interlocking of the tab and the immediate underlying slot.

As used herein, the term "slot" designates any slit, cut or narrow opening, with simple slits being particularly preferred for application in the present invention. The expression "forced bypass locking" is used to designate a locking system wherein the locking tab overlies the receiving locking slot, and the opposite sides of the slot are displaced in a direction normal to the plane of the folder until the end of the tab bypasses the opposing edge of the slot and gains entry to the opened slot. Forced bypass locking is contrasted to the method of locking wherein a tab is inserted tip first into a receiving slot. Forced bypass locking has an advantage over tab insertion in that precise alignment of the tip of the tab with the opening of the slot is not required, and locking is achieved quickly and surely by the application of line forces in a single direction normal to the plane of the folder at each locking position. The method is thus readily adaptable to rapid manual or automatic machine closure.

Folders may be constructed of any relatively stiff, foldable, card-like material including paper, paperboard, plastic and laminates of these with paper, plastic, fabric, or foil sheets. A particularly preferred foldable preferred foldable material is a paperboard such as 5 point to 12 point solid bleached sulfate board.

Referring now to the drawigs, FIG. 1 illustrates a section of a typical three-panel folder having two locking tabs in accordance with the present invention. The folder is comprised of center panel Y and two end panels X and Z. Panels X and Z are adapted to be folded inwardly over panel Y along lines 10 and 11, respectively, with panel X underlying outer panel Z as illustrated in FIG. 2. Panel Z is provided with two tabs extending beyond the panel edge identified in FIG. 1 as C and C'. The tabs are preferably of a curvilinear design as shown but may also be rectangular, triangular or of other configuration, the particular shape of the tab not being critical to the present invention.

Referring further to FIG. 1, center panel Y is provided with relief slots B and B' corresponding to tabs C and C', respectively, and located distance $d_1$ from the fold line between panels Y and Z, distance $d_1$ being approximately equal to distance $d_1'$, the measure of the distance from the tip of tab C to the fold line between panels Y and Z. Thus, when the folder is in its folded configuration as shown in FIG. 2, the tip of tab C is substantially aligned with relief slot B in panel Y.

Underlying panel X is provided with locking slots A and A' corresponding to tabs C and C', respectively. Locking slot A is located at distance $d_3$ from the fold line between panels X and Y, $d_3$ being the distance equal to the difference between the width of panel Y shown as $d_4$ and the distance from the fold line betwee panels Y and Z to a point on tab C corresponding to the intended line of intersection between tab C and slot A in the locked configuration. The portion of the tab lying between $d_1$ and $d_2$ is the portion intended to be contained within slot A when the folder is in the locked configuration as shown in FIG. 2.

The relative positions of slots A and B and tab C after locking are readily apparent from FIG. 2 which shows the folder in its folded and locked configuration with tab C interlocked with slot A.

The folder may, in addition to slots A and B, contain relief slot D located between slots A and B and along the fold line of panels X and Y as shown in FIG. 1. The function of relief slot D is to relieve stress in the area of the locking tabs to facilitate the displacement of slots A and B in a direction normal to the plane of the folder during the forced bypass locking operation. Relief slot D is optional and may be omitted as illustrated in FIG. 1 by a continuous fold line between slots A' and B'.

The method of forced bypass locking and the functional relationships between slots A and B and tab C during locking is illustrated in FIG. 3 which presents a series of cross-sectional views of the folder of FIG. 2 taken on line 3—3 through locking means A', B' and C'. FIG. 3(a) shows the folder in a folded configuration prior to locking. FIG. 3(b) shows the displacements of slots A' and B' in a plane normal to the plane of the folder with tab C' being forcibly directed toward bypassing the opposing edge of slot A'. Relief slot B' facilitates the displacement of slot A' to assist in the forced bypassing of tab A'. FIG. 3(c) shows slots A' and B' fully displaced with locking tab C' already forced passed the outer edge of slot A'. FIG. 3(d) shows the folder with tab C' securely interlocked with slot A' after the force used to displace slots A' and B' has been removed and slot B' has returned to its intitial flat position to preserve the substantially smooth surface of panel Y.

The locking tab and slot with relief slot combination of the present invention can be used wherever desired to mechanically lock a paper board or like material in a folded construction. One particularly preferred application is in the construction of suture packages such as the long package illustrated in FIG. 4 where the body of the package is secured with the integral locking means of the present invention. The suture package is provided with needle window flaps 16 and 17 and cover flap 12 having tab 13 adapted to be inserted in slot 14 to effect closure of the needle window. Sutures 15 are contained within the package with needles displayed in the needle window for ready removal of the suture once the package is opened.

Although the preceding description of the present invention has been directed to three-panel folders for convenience of explanation, it will be readily appreciated that the locking means disclosed herein can also be employed with folders having four or more panels if desired. In such folders, the locking slots corresponding to slot A in panel X are provided in the panel immediately underlying the outer end panel corresponding to panel Z having the locking tab corresponding to tab C. All remaining panels not interlocking with tab C are provided with relief slots superimposed with corresponding slot B in panel Y. One such folder is illustrated in FIGS. 5, 6 and 7 where end panel X consists of four panels in a folded relationship. The panel of X destined to underlie panel Z is providing with locking slot A while the remaining panels of X not intended to interlock with tab C are provided with relief slots B'' which are in alignment with relief slot B in panel Y when panel X is folded over panel Y. The completely folded and locked package is illustrated in FIG. 7.

Many variations in folder construction which nevertheless employ the forced bypass locking means of the present invention will be evident to those skilled in the art. For example, the locking means of the present invention may be used in conjunction with adhesives or additional mechanical securing means. Folders employing the locking means of the present invention may also include a variety of other tabs, slots, cut-outs, cover-flaps, end-flaps and the like. All such variations are accordingly included within the scope of the present invention.

What is claimed is:

1. A folder of a stiff, foldable material comprising at least three adjacent panels foldably connected and including a center panel and two end panels, said end panels being folded inwardly over said center panel to provide an outer end panel partially overlapping an underlying end panel, and integral locking means for maintaining said panels in said folded construction, said locking means comprising a tab on the outer end panel extending beyond the edge of said panel, a locking slot in the underlying end panel underlying said tab and adapted to receive said tab, and a relief slot in the center panel substantially aligned with the tip of said tab whereby said tab may be forced to bypass the opposing edge of said locking slot and gain entry to said slot by displacing the edges of the locking slot and the relief slot in a direction normal to the plane of the folder.

2. A folder of claim 1 wherein the folder material is paper or paperboard.

3. A folder of claim 1 having a plurality of locking means along the edge of the outer end panel.

4. A folder of claim 1 wherein the locking tab is curvilinear in shape.

5. A suture package comprising a folder of claim 1 containing at least one surgical suture between the folded panels.

6. A folder of a stiff, foldable material comprising at least three adjacent panels foldably connected and including a center panel and two end panels, said end panels being folded inwardly over said center panel to provide an outer end panel partially overlapping an underlying end panel, the underlying panel comprising a plurality of foldably connected inner panels, and integral locking means for maintaining said panels in said folded construction, said locking means comprising a tab on the outer end panel extending beyond the edge of said panel, a locking slot in the underlying end panel underlying said tab and adapted to receive said tab, and a relief slot in the center panel and each of said inner panels of said underlying end panel substantially aligned with the tip of said tab whereby said tab may be forced to bypass the opposing edge of said locking slot and gain entry to said slot by displacing the edges of the locking slot and the relief slots in a direction normal to the plane of the folder.

* * * * *